United States Patent [19]

Pracht et al.

[11] 4,233,451
[45] Nov. 11, 1980

[54] PROCESS FOR MAKING IMIDAZOLINIUM SALTS

[75] Inventors: Hans J. Pracht, Sycamore Township, Hamilton County; Joseph P. Nirschl, Fairfield, both of Ohio

[73] Assignee: The Procter & Gamble Company, Cincinnati, Ohio

[21] Appl. No.: 953,065

[22] Filed: Oct. 20, 1978

Related U.S. Application Data

[60] Division of Ser. No. 708,980, Jul. 27, 1976, Pat. No. 4,127,489, which is a continuation-in-part of Ser. No. 687,951, May 20, 1976, abandoned.

[51] Int. Cl.$^3$ .......................................... C07D 233/24
[52] U.S. Cl. ..................................... 548/354; 548/352
[58] Field of Search .............................. 548/354, 352

[56] References Cited

U.S. PATENT DOCUMENTS

| 23,227 | 5/1950 | Blair . | |
|---|---|---|---|
| 2,211,001 | 8/1940 | Chwala | 548/352 |
| 2,267,965 | 12/1941 | Wilson | 548/352 |
| 2,468,180 | 4/1949 | Groote | 548/352 |
| 2,713,582 | 7/1955 | Smith . | |
| 2,794,808 | 6/1957 | Albrecht | 548/354 |
| 2,920,043 | 1/1960 | Burns | 548/354 |
| 2,971,006 | 2/1961 | Mayhew | 548/354 |
| 3,056,688 | 10/1962 | Olney | 548/352 |
| 3,244,724 | 4/1966 | Guttmann . | |
| 3,736,098 | 5/1973 | Katoaka et al. | 548/352 |
| 3,749,691 | 7/1973 | Kandathil . | |
| 3,776,844 | 12/1973 | Nayfa . | |
| 3,819,539 | 6/1974 | Bloch et al. . | |
| 3,849,435 | 11/1974 | Diery | 548/354 |
| 3,855,235 | 12/1974 | McConnell . | |
| 3,887,476 | 6/1975 | McConnell . | |
| 3,933,871 | 1/1976 | Armstrong . | |
| 4,109,094 | 8/1978 | Trivedi et al. | 548/354 |

OTHER PUBLICATIONS

Kytides et al., Jour. of Org. Chem. 12:577–586, 1947.
Shepard et al., Journal of the American Chem. Soc. 69:2269–2270, (1947).

*Primary Examiner*—Henry R. Jiles
*Assistant Examiner*—Jane T. Fan
*Attorney, Agent, or Firm*—Ronald L. Hemingway; Richard C. Witte

[57] ABSTRACT

A process for making quaternary imidazolinium fabric conditioning agents essentially free of amines, amine salts and alkoxylated forms of the quaternary imidazolinium salts. An aqueous liquid fabric conditioning composition containing quaternary imidazolinium conditioning agents essentially free of amines and amine salts possesses desirable stability and conditioning properties.

18 Claims, No Drawings

PROCESS FOR MAKING IMIDAZOLINIUM SALTS

CROSS-REFERENCE TO RELATED APPLICATION

This application is a division of application Ser. No. 708,980, filed July 27, 1976, now U.S. Pat. No. 4,127,489, issued Nov. 28, 1978 which is a continuation-in-part of application Ser. No. 687,951, filed May 20, 1976, now abandoned.

BACKGROUND OF THE INVENTION

This invention relates to the production of quaternary imidazolinium fabric conditioning agents essentially free of amines, amine salts and alkoxylated forms of the quaternary imidazolinium salts. The present invention additionally relates to a fabric conditioning composition containing an imidazolinium agent essentially free of amines and amine salts and a method for conditioning fabrics.

In the conventional home laundering process, soiled fabrics are subjected to cleaning with a detergent composition in the main wash cycle and rinsing with water in the final cycle. Optionally, during the rinsing cycle a fabric conditioning composition is added. Such compositions contain a fabric softener or fabric antistat material for imparting to the rinsed fabrics softening and antistat properties. The rinsed fabrics are oftentimes, thereafter, dried in an automatic clothes dryer.

Many different types of fabric conditioning agents have been used in rinse cycle added fabric conditioning compositions. The most favored type of agent has been the quaternary ammonium compounds. These compounds may take the form of noncyclic quaternary ammonium salts having preferably two long chain alkyl groups attached to the nitrogen atom. Additionally, imidazolinium salts have been used by themselves or in combination with other agents in the treatment of fabrics. U.S. Pat. No. 2,874,074, Feb. 17, 1959, to Johnson discloses using imidazolinium salts to condition fabrics. U.S. Pat. No. 3,681,241, Aug. 1, 1972, to Rudy, and U.S. Pat. No. 3,033,704, May 8, 1962, to Sherrill et al. disclose fabric conditioning compositions containing mixture of imidazolinium salts and other fabric conditioning agents.

While the prior art shows the use of quaternary imidazolinium salts as fabric conditioning agents, it is silent about the problems encountered in making stable fabric conditioning compositions containing such agents and aldehydes. The manufacture of imidazolinium salts generally involves the reaction of a polyamine with an acyl containing material such as an acid or ester to form an imidazoline and then a quaternizing of the imidazoline. U.S. Pat. Nos. 2,355,837, Aug. 15, 1974, and 2,267,965, Dec. 30, 1941, to Wilson; and U.S. Pat. No. 2,520,102, Aug. 22, 1950, to Tryon, all disclose methods for making imidazolines used in making imidazolinium salts. It has been found in the present invention that in addition to the imidazoline compound formed in the described reaction, primary and secondary amines are also present. During the subsequent quaternization step, these amines cause some of the imidazoline compound to form the imidazoline amine salt rather than the quaternary imidazolinium salt. The imidazoline amine salt, when present in an aqueous medium having a near neutral or higher pH, is capable of undergoing ring opening to form free amines which will then react with aldehydic compounds in the composition much the same as free amines which have not been converted to the salt form. The result is that the odor of the composition degrades (perfumes generally contain aldehydes), the color and the pH change and aldehyde preservatives degrade. The aforementioned Johnson patent describes making quaternary imidazolinium salts, but is silent about how to overcome the problems described while still achieving an end product which is sufficiently high in imidazolinium salt to be commercially attractive. In the process aspect of the present invention the undesirable amines are "capped" using an alkoxylating agent in an amount sufficient to cap the primary and secondary amines but not cap to any appreciable degree the cyclic tertiary amine which forms the imidazolinium salt.

It is, therefore, an object of this invention to provide a process for making quaternary imidazolinium salts which are essentially free of amines, amine salts and alkoxylated forms of the imidazolinium salts.

It is another object of this invention to provide a fabric conditioning composition comprising a quaternary imidazolinium salt and being essentially free of amines and amine salts.

It is still another object of this invention to provide a method for conditioning fabrics by treating them with the desired imidazolinium salts.

These and other objects will become apparent from the description which follows.

As used herein all percentages and ratios are by weight unless otherwise specified.

SUMMARY OF THE INVENTION

The present invention encompasses in one aspect a process for making imidazolinium salts having the following formula:

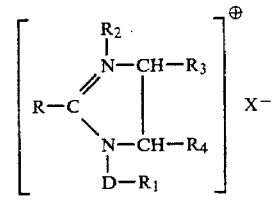

wherein R and $R_1$ are aliphatic or cycloaliphatic hydrocarbon groups containing from about 10 to about 22 carbon atoms; D is a divalent nonamino organic radical containing from about 1 to about 20 carbon atoms and is composed of elements selected from the group consisting of C, O, N and H. X is an anion; $R_2$ is an alkyl, substituted alkyl or aralkyl group containing from about 1 to about 8 carbon atoms. $R_3$ and $R_4$ are hydrogen, hydroxy, a short chain alkyl having from 1 to 4 carbon atoms or hydroxy forms of the short chain alkyl. In an optional form D may be absent and $R_1$ attached directly to the number 1 nitrogen in the ring. In another option, $R_1$ and D may be absent and in their place a group from the imidazoline forming amine may be present. The imidazolinium salts are essentially free of amines, amine salts and alkoxylated forms of the imidazolinium salts. It is to be appreciated that while the $R_2$ group is shown as being on the number 3 nitrogen, it may also be present on the number 1 nitrogen.

The invention also encompasses a fabric conditioning composition comprising a quaternary imidazolinium salt which is essentially free of amines and amine salts. Methods of conditioning fabrics with the imidazolinium salts are also provided.

DETAILED DESCRIPTION OF THE INVENTION

In accordance with this invention, quaternary imidazolinium salts essentially free of amines, amine salts and alkoxylated forms of the imidazolinium salts are produced.

The reaction to form the desired imidazolinium salt involves the following steps:

Formation of Imidazoline

The imidazoline precursor for the desired imidazolinium salt is formed by reacting acylating or esterifying agents with alkylene or polyalkylene polyamines having two or three amino groups, one of which is a primary or secondary amino group in the 2 position to a primary amino group. The reaction is conducted at a temperature of about 100° C. to about 250° C. for a period of about 3 to about 24 hours, at a molar ratio of acyl groups to primary amine and hydroxyl groups ranging from about 0.33:1 to about 1.5:1, preferably from about 1:1 to about 1.5:1, and under reflux or at atmospheric pressure or slightly greater. To facilitate the formation of the imidazoline ring structure the reaction mixture may subsequently be subjected to a vacuum of from about 0.4 to about 10 mm of mercury for a period of from about 1 to about 8 hours. The resulting mixture contains in addition to the desired imidazoline some of the original acylating material, some of the original polyamine, some of the noncyclized intermediate amide products and other mixed reaction products. The acylating or esterifying agent may be any acid or other acyl containing compound having an aliphatic or cycloaliphatic hydrocarbon group of about 10–22 carbon atoms. Examples of such materials include the fatty acids lauric, decanoic, undecanoic, dodecanoic, tridecanoic, myristic, pentadecanoic, hexadecanoic, palmitic and the like. Preferred fatty acids are the mixtures thereof derived from tallow, soybean or coconut oils. Particularly preferred are the soft or hardened tallow fatty acids. Other acylating or esterifying agents include the alkyl esters of the fatty acids and the naturally occurring glyceride esters. The latter are preferred for use herein.

The polyamine material, as indicated above, has either two or three amino groups wherein one is a primary or secondary amino group in the 2 position to a primary amine group. These preferably take the following form:

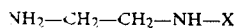

NH$_2$—CH$_2$—CH$_2$—NH—X where X may be, for example, hydrogen, $-\!(CH_2-CH_2)_n-\!NH_2$, $-\!(CH_2-CH_2)_n-\!OH$ or $-\!(CH_2-CH_2)_n-\!CH_3$ wherein n is from 1 to about 6. Examples of such polyamines include diethylenetriamine, ethylenediamine, hydroxyethyl ethylenediamine, etc.

Addition of Second Long Chain Alkyl or Substituted Alkyl Group

As described above, the formation of the imidazoline is accomplished by reacting a polyamine with an acylating or esterifying agent. If the amount of acylating or esterifying agent used is not sufficient to form an amide or ester with at least two of the amine or hydroxyl groups present in the polyamine (the molar ratio of acyl groups to primary amine or hydroxyl groups being from about 0.33 to about 0.66), the imidazoline formed will only have a long chain group of the type desired positioned at the 2 position rather than at both the 1 and 2 positions of the imidazoline ring. The mono substituted material then has to be reacted further with an acylating or esterifying agent. The reaction temperature is generally the same as the generalized reaction given above while the molar ratio of acylating agent or esterifying agent to mono substituted imidazoline ranges from about 1:1 to about 1.5:1 and the reaction time ranges from about 1 to about 24 hours. Optionally, a vacuum of from about 0.4 to about 10 mm of mercury is drawn. This reaction can be exemplified as follows using diethylenetriamine as the polyalkylene polyamine:

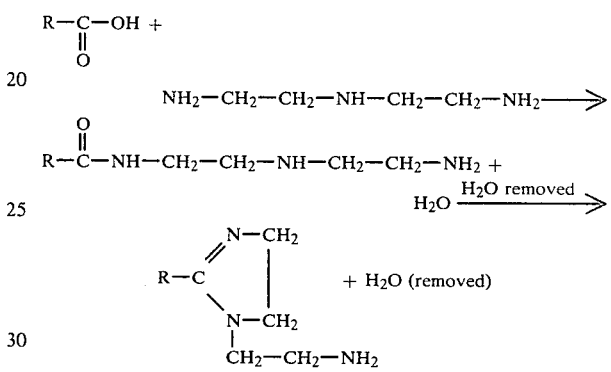

where R is an aliphatic or cycloaliphatic hydrocarbon group containing from about 10 to about 22 carbon atoms.

The primary amine present in the imidazoline formed above then has to be converted to an amide to attach the second long chain R group in the following manner:

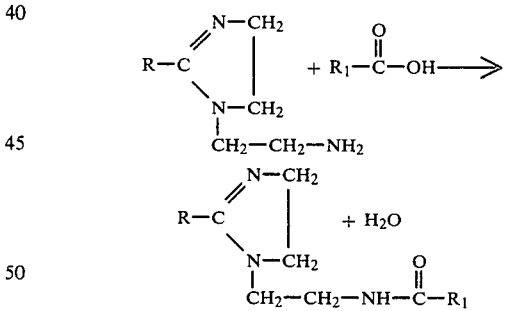

where R$_1$ is an aliphatic or cycloaliphatic hydrocarbon group containing from about 10 to about 22 carbon atoms. The group

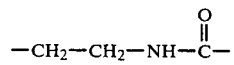

in the above formula corresponds to D in the formula given above in the Summary of the Invention section. It should be appreciated that D may be another divalent radical or absent depending on the choice and concentration of polyamine and acylating or esterifying agent. See, for example, U.S. Pat. No. 2,267,965 to Wilson, mentioned previously, where an hydroxy group is attached to the 1 position of the imidazoline ring. Also the other U.S. Patent to Wilson mentioned previously, U.S. Pat. No. 2,355,837, for other polyamines.

Of course, if the amount of acylating or esterifying agent used contains a number of acylating groups sufficient to form an amide or ester with at least two of the amine or hydroxyl groups (ratio of acyl to primary amine or hydroxyl groups is from about 0.67 to about 1.5:1, preferably 1:1 to about 1.1:1), the long chain group in the 1 position would be present as a result of the initial imidazoline forming reaction. The following represents such a reaction:

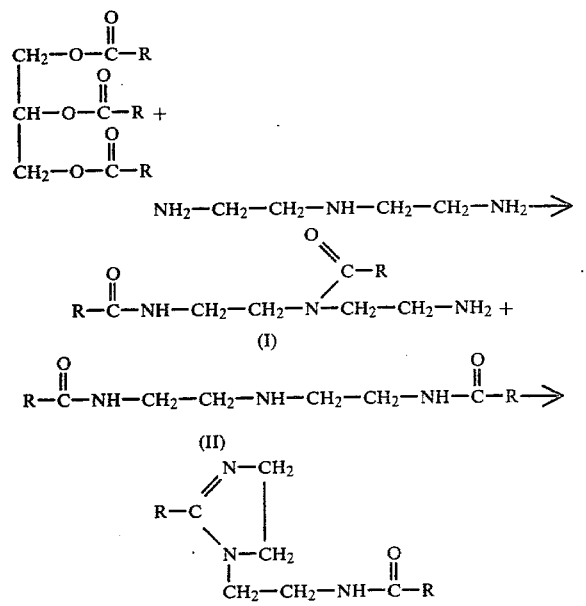

Some of the intermediate amides shown above, as well as some of the starting materials, other intermediates, water and other complexes are present as diluents along with the desired substituted imidazoline. Some of the diluents are removed during the vacuum stage of the reaction.

Alkoxylation of Imidazoline

The formation of the 1,2 substituted imidazoline product will have as components in addition to the desired imidazoline product the materials noted as diluents in the glyceride reaction above. If the imidazoline reaction formation is the fatty acid reaction given above wherein the 2 substituted imidazoline is formed first and then the second long chain aliphatic or cycloaliphatic hydrocarbon group is added in the 1 position by means of a reaction with a fatty acid, or other agent, the desired imidazoline is going to be present in a mixture containing some of the imidazoline substituted only at the 2 position and fatty acid or other agent. Similarly, regardless of which reaction route is used, there will be primary and/or secondary amines present in the final mixture due to either unreacted initial amine or the amide intermediate products. The materials which have primary and secondary amine groups present are undesirable since in the quaternizing step, to be discussed subsequently, the amines cause the disubstituted imidazoline to be transformed to an amine salt rather than a quaternary salt which, in turn, is capable of reverting to free amines when present in an aqueous composition having a pH of about 5 or greater. The patent issued to Johnson, U.S. Pat. No. 2,874,074, Feb. 17, 1959, mentioned earlier in this application, discloses making the 1,2 substituted imidazoline by the two step fatty acid process. Johnson utilizes the 2 substituted imidazoline as made by Wilson, U.S. Pat. No. 2,355,837, Aug. 15, 1944, or U.S. Pat. No. 2,267,965, Dec. 30, 1941. The imidazoline product as made by Johnson would contain a mixture of the 1,2 substituted material, the 2 substituted material, other amine containing materials and fatty acid. The 2 substituted material and the other amines are undesirable, as indicated above, due to their ability to cause the imidazoline salt to be formed.

The present applicants have found that the undesirable amine products present in the 1,2 substituted imidazoline reaction mixture can be effectively capped by treating the mixture with an alkylene oxide, preferably propylene oxide. The alkylene oxide serves to "cap" the amines by attaching an alkylene oxide moiety to the free amine. It is important that all of the primary and secondary amines are capped, but only a minimum of the tertiary amine in the imidazoline. To achieve these goals the mixture containing the desired 1,2 substituted imidazoline is treated with an amount of an alkylene oxide amounting to from about 1 to 5% by weight of the mixture to be treated, while the temperature is kept at from about 80° C. to about 140° C. and a vacuum is optionally drawn amounting to from about 2 to about 15 mm mercury. The vacuum helps to rid the system of excess alkylene oxide, polyamine and other low boiling diluents. The imidazoline containing mixture can also be diluted with an organic solvent such as isopropyl alcohol or glymes to facilitate the alkylene oxide treatment. Such solvents are used in an amount of from about 1 to about 25% by weight of the imidazoline mixture. The time of the reaction ranges from about 0.5 to about 8 hours. U.S. Pat. No. 2,713,582, July 19, 1955, to Smith, discloses making fully alkoxylated imidazolines as a precursor for carboxylate detergent products. Examples of alkoxylating agents other than propylene oxide include butylene oxide, glycide, ethylene oxide, cyclohexame oxide, etc.

Quaternization

The alkylene oxide treated mixture from above is treated with an alkylating agent to form the desired quaternary imidazolinium material essentially free of amines, amine salts and alkoxylated forms of the imidazolinium salts. The imidazolinium product preferably contains a total less than about 4%, preferably less than about 2%, of primary amines, secondary amines and cyclic tertiary amine salts and less than about 25%, preferably 4%, of the alkoxylated form of the imidazolinium salt. The limit on the alkoxylated form is the result of wanting to make the nonalkoxylated imidazolinium salt as pure as possible and is not related to the amine/amine salt stability problem. The alkylating agent can be any of the known agents such as methylchloride, ethylbromide, diethylsulfate, dimethylsulfate, hexadecylchloride, among many others. The reaction can be exemplified in the following manner:

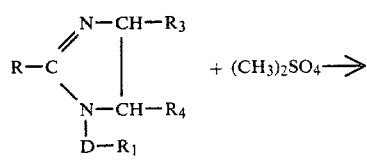

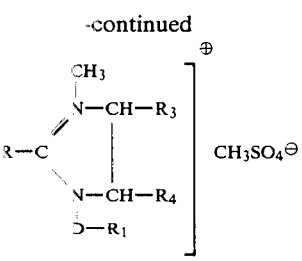

wherein D, R, R₁, R₃ and R₄ are as described previously.

The amount of alkylating agent used should be equivalent to the amount of the imidazoline treated on a molar basis. However, an excess of the alkylating agent is generally used to assure maximum quaternization. The amount of excess employed should be sufficient so that the pH of the reaction medium is in the range of from about 5 to about 7. The reaction time generally ranges from about 1 to about 12 hours and the temperature from about 40° to about 80° C. If desired, a base may be added during the alkylation to aid quaternization.

The imidazolinium salt as formed above has outstanding fabric conditioning properties, softening and antistatic, while additionally allowing fabric conditioning compositions to be made which have improved aldehyde stability. A preferred imidazolinium salt contains R₁ and R groups having 14–20 carbon atoms such as the following wherein the R groups are tallow cuts:

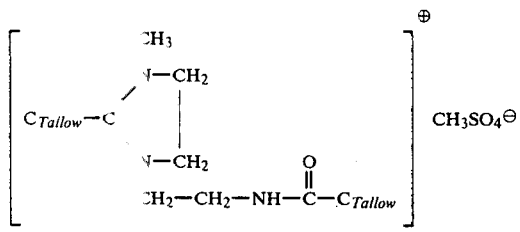

wherein $C_{Tallow}$ is an aliphatic hydrocarbon chain derived from tallow fatty acid.

Other quaternary imidazolinium salts having desirable properties can be formed by substituting a different R group for tallow in the acylating or esterifying agent, a different alkylene or polyalkylene polyamine for diethylenetriamine, and a different alkyl, substituted alkyl or aralkyl for the methyl group present, as well as a different anion, in the alkylating agent.

Fabric Conditioning Compositions

The present invention is also directed to compositions comprising 1,2 substituted quaternary imidazolinium salts, said compositions containing a total less than about 4%, preferably less than about 2%, of primary amines, secondary amines and cyclic tertiary amine salts based on the weight of the imidazolinium salt. Additionally, the compositions preferably contain less than about 25%, more preferably less than about 4%, of the alkoxylated form of the imidazolinium salt based on the weight of the nonalkoxylated form of the imidazolinium salt. The desired imidazolinium salt can be prepared using the process previously described, or another process which will yield the imidazolinium salt and will not have more than the above indicated levels of the various undesirable compounds. As indicated earlier, the imidazolinium compounds of interest herein have the formula:

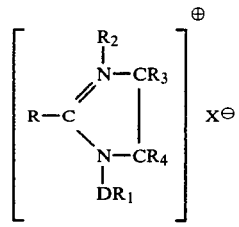

wherein D is an nonamino divalent organic radical containing from 1 to about 20 carbon atoms comprised of elements selected from C, H, N and O. R and R₁ are aliphatic or cycloaliphatic hydrocarbon groups having from about 10 to about 22 carbon atoms. R₃ and R₄ are hydrogen, hydroxyl, short chain alkyl having from 1 to 4 carbon atoms or hydroxy forms of the short chain alkyl. Examples of D are

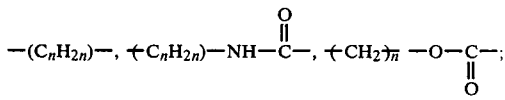

among many others, where n is a number from 1 to about 6. R₂ is an alkyl, substituted alkyl or aralkyl having from about 1 to 8 carbon atoms, which was associated with the alkylating agent used to quaternize the imidazoline compound. Examples of such cations are methyl, ethyl, benzyl, etc. X is an anion associated with the alkylating agent and may be, for example, chloride, bromide, methylsulfate, ethylsulfate, among others. It is to be recognized that while the quaternization is indicated as having taken place at 3-nitrogen, quaternization at the 1-nitrogen atom is not excluded. A preferred quaternary imidazolinium salt is the methylsulfate salt shown above.

The compositions of the present invention are preferably aqueous and may contain any desired level of the quaternary imidazolinium salt. However, the compositions preferably contain from about 1 to about 15% of the salt and most preferably from about 2 to about 8%.

In addition to the preferred quaternary imidazolinium salt, the compositions of the present invention may also contain other fabric conditioning (softening/antistatic) agents. Such other agents may be described as cationic and nonionic organic materials which are free of primary amines, secondary amines and cyclic tertiary amine salts and are generally employed as fabric conditioning agents during the rinsing cycle of the household laundering process. They are organic, waxy materials having a melting (or softening) point between 25° C. and 115° C. Such materials possess both fabric softening and fabric antistat properties.

Generally the cationic nitrogen-containing compounds such as quaternary ammonium compounds have one or two straight-chain organic groups of at least eight carbon atoms. Preferably, they have one or two such groups of from 12 to 22 carbon atoms. Preferred cation-active softener compounds include the quaternary ammonium antistat/softener compounds corresponding to the formula:

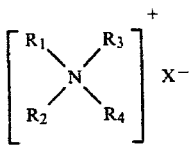

wherein $R_1$ is hydrogen or an aliphatic group of from 1 to 22 carbon atoms; $R_2$ is an aliphatic group having from 12 to 22 carbon atoms; $R_3$ and $R_4$ are each alkyl groups of from 1 to 3 carbon atoms; and X is an anion selected from halogen, acetate, phosphate, nitrate and methyl sulfate radicals.

Because of their excellent softening efficacy and ready availability, preferred cationic antistatic/softener compounds of the invention are the dialkyl dimethyl ammonium chlorides, wherein the alkyl groups have from 12 to 22 carbon atoms and are derived from long-chain fatty acids, such as hydrogenated tallow. As employed herein, alkyl is intended as including unsaturated compounds such as are present in alkyl groups derived from naturally occurring fatty oils. The term "tallow" refers to fatty alkyl groups derived from tallow fatty acids. Such fatty acids give rise to quaternary softener compounds wherein $R_1$ and $R_2$ have predominantly from 16 to 18 carbon atoms. The term "coconut" refers to fatty acid groups from coconut oil fatty acids. The coconut-alkyl $R_1$ and $R_2$ groups have from about 8 to about 18 carbon atoms and predominate in $C_{12}$ to $C_{14}$ alkyl groups. Representative examples of quaternary softeners of the invention include tallow trimethyl ammonium chloride; ditallow dimethyl ammonium chloride; ditallow dimethyl ammonium methyl sulfate; dihexadecyl dimethyl ammonium chloride; di(hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium methyl sulfate; dihexadecyl diethyl ammonium chloride; dihexadecyl dimethyl ammonium acetate; ditallow dipropyl ammonium phosphate; ditallow dimethyl ammonium nitrate; di(coconut-alkyl) dimethyl ammonium chloride.

An especially preferred class of quaternary ammonium antistat/softeners of the invention correspond to the formula:

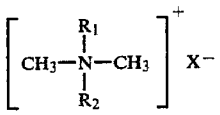

wherein $R_1$ and $R_2$ are each straight chain aliphatic groups of from 12 to 22 carbon atoms and X is halogen, e.g., chloride or methyl sulfate. Especially preferred are ditallow dimethyl ammonium chloride and di(hydrogenated tallow-alkyl) dimethyl ammonium chloride and di(coconut-alkyl) dimethyl ammonium chloride, these compounds being preferred from the standpoint of excellent softening properties and ready availability.

Nonionic fabric antistat/softener materials include a wide variety of materials including sorbitan esters, fatty alcohols and their derivatives and the like. One preferred type of nonionic fabric antistat/softener material comprises the esterified cyclic dehydration products of sorbitol, i.e., sorbitan ester. Sorbitol, itself prepared by catalytic hydrogenation of glucose, can be dehydrated in well-known fashion to form mixtures of cyclic 1,4- and 1,5-sorbitol anhydrides and small amounts of isosorbides. (See Brown; U.S. Pat. No. 2,322,821; issued June 29, 1843) The resulting complex mixtures of cyclic anhydrides or sorbitol are collectively referred to herein as "sorbitan". It will be recognized that this "sorbitan" mixture will also contain some free uncyclized sorbitol.

Sorbitan ester fabric antistat/softener materials useful herein are prepared by esterifying the "sorbitan" mixture with a fatty acyl group in standard fashion, e.g., by reaction with a fatty ($C_{10}$–$C_{24}$) acid or fatty acid halide. The esterification reaction can occur at any of the available hydroxyl groups, and various mono-, di-, etc., esters can be prepared. In fact, complex mixtures of mon-, di-, tri-, and tetra-esters almost always result from such reactions, and the stoichiometric ratios of the reactants can simply be adjusted to favor the desired reaction product.

The foregoing complex mixtures of esterified cyclic dehydration products of sorbitol (and small amounts of esterified sorbitol) are collectively referred to herein as "sorbitan esters". Sorbitan mono- and di-esters of lauric, myristic, palmitic, stearic and behenic acids are particularly useful herein for conditioning the fabrics being treated. Mixed sorbitan esters, e.g., mixtures of the foregoing esters, and mixtures prepared by esterifying sorbitan with fatty acid mixtures such as the mixed tallow and hydrogenated palm oil fatty acids, are useful herein and are economically attractive. Unsaturated $C_{10}$–$C_{18}$ sorbitan esters, e.g., sorbitan mono-oleate, usually are present in such mixtures. It is to be recognized that all sorbitan esters, and mixtures thereof, which are essentially water-insoluble and which have fatty hydrocarbyl "tails", are useful fabric antistat/softener materials in the context of the present invention.

The preferred alkyl sorbitan ester fabric antistat/softener materials herein comprise sorbitan monolaurate, sorbitan monomyristate, sorbitan monopalmitate, sorbitan monostearate, sorbitan monobehenate, sorbitan dilaurate, sorbitan dimyristate, sorbitan dipalmitate, sorbitan distearate, sorbitan dibehenate, and mixtures thereof, the mixed coconutalkyl sorbitan mono- and di-esters and the mixed tallowalkyl sorbitan mono- and di-esters. The tri- and tetra-esters of sorbitan with lauric, myristic, palmitic, stearic and behenic acids, and mixtures thereof, are also useful herein.

Another useful type of nonionic fabric antistat/softener material encompasses the substantially water-insoluble compounds chemically classified as fatty alcohols. Mono-ols, di-ols, and poly-ols having the requisite melting points and water-insolubility properties set forth above are useful herein. Such alcohol-type fabric conditioning materials also include the mono- and di-fatty glycerides which contain at least one "free" OH group.

All manner of water-insoluble, high melting alcohols (including mono- and di-glycerides), are useful herein, inasmuch as all such materials are fabric sustantive. Of course, it is desirable to use those materials which are colorless, so as not to alter the color of the fabrics being treated. Toxicologically acceptable materials which are safe for use in contact with skin should be chosen.

A preferred type of unesterified alcohol useful herein includes the higher melting members of the so-called fatty alcohol class. Although once limited to alcohols obtained from natural fats and oils, the term "fatty alcohols" has come to mean those alcohols which correspond to the alcohols obtainable from fats and oils, and all such alcohols can be made by synthetic processes. Fatty alcohols prepared by the mild oxidation of petroleum products are useful herein.

Another type of material which can be classified as an alcohol and which can be employed as a fabric antistat/softener material in the instant invention encompasses various esters of polyhydric alcohols. Such "ester-alcohol" materials which have a melting point within the range recited herein and which are substantially water-insoluble can be employed herein when they contain at least one free hydroxyl group, i.e., when they can be classified chemically as alcohols.

The alcoholic di-esters of glycerol useful herein include both the 1,3-di-glycerides and the 1,2-di-glycerides. In particular, di-glycerides containing two $C_8$-$C_{20}$, preferably $C_{10}$-$C_{18}$, alkyl groups in the molecule are useful fabric conditioning agents.

Non-limiting examples of ester-alcohols useful herein include: glycerol-1,2-dilaurate; glycerol-1,3-dilaurate; glycerol-1,2-myristate; glycerol-1,3-dimyristate; glycerol-1,2-dipalmitate; glycerol-1,3-dipalmitate; glycerol-1,2-distearate and glycerol-1,3-distearate. Mixed glycerides available from mixed tallowalkyl fatty acids, i.e., 1,2-ditallowalkyl glycerol and 1,3-ditallowalkyl glycerol, are economically attractive for use herein. The foregoing ester-alcohols are preferred for use herein due to their ready availability from natural fats and oils.

Mono- and di-ether alcohols, especially the $C_{10}$-$C_{18}$ di-ether alcohols having at least one free —OH group, also fall within the definition of alcohols useful as fabric antistat/softener materials herein. The ether-alcohols can be prepared by the classic Williamson ether synthesis. As with the ester-alcohols, the reaction conditions are chosen such that at least one free, unetherified -OH group remains in the molecule.

Ether-alcohols useful herein include glycerol-1,2-dilauryl ether; glycerol-1,3-distearyl ether; and butane tetra-ol-1,2,3-trioctanyl ether.

The fabric antistat/softeners mentioned above can be used alone or as mixtures in combination with the imidazolinium compound in the practice of the present invention. The agents when present in the compositions of the present invention are normally present in amount ranging from about 1 to 12% by weight of the composition, preferably from about 1 to about 8%. Preferred mixtures are mixtures of the quaternary imidazolinium salt with a sorbitan ester, a fatty alcohol, or a quaternary ammonium compound. A most preferred mixture is the quaternary imidazolinium salt with ditallow dimethyl ammonium chloride (DTDMAC). These two compounds are preferably used in a weight ratio of from about 80/20 to about 20/80 and most preferably in a weight ratio of from 30/70 to 70/30 imidazolinium/DTDMAC.

Conventional liquid fabric conditioning composition components may be dissolved or dispersed in the composition. These conventional components include clay materials, aldehyde preservatives, emulsifiers, thickeners, opacifiers, coloring agents, brighteners, fluorescers, pH adjustment agents and perfume materials. Such optical materials generally comprise about 0.01% to 10% by weight of the composition.

Processing

The aqueous fabric conditioning compositions herein can be prepared by adding the fabric softening and static control agents to water using conventional techniques. For example, the agent or agents can be heated to form a liquid oily phase and can be added with mixing to water maintained at elevated temperatures. Optional ingredients can be added according to methods known in the art. The composition is then adjusted to a pH of from about 3 to about 9, preferably from about 4.5 to 7.

Composition Usage

The compositions of the present invention are preferably used in the rinse cycle of the conventional automatic laundry operations. Generally, rinse water has a temperature of from about 15° C. to about 60° C.

When compositions of the present invention are added to the rinse cycle, the fabric conditioning agents are generally present at levels of from about 2 ppm to about 500 ppm, preferably from about 10 ppm to about 100 ppm. These concentration levels achieve superior fabric softening and static control.

In general, the invention herein in its fabric conditioning method aspect comprises: (a) washing fabrics in a conventional automatic washing machine with a detergent composition (normally containing a detersive surfactant or mixture of surfactants selected from the group consisting of anionic, nonionic, amphoteric or ampholytic surfactants), (b) rinsing the fabrics, and (c) adding during the rinse stage of the operation the above-described levels of the fabric conditioning agents. Preferably, a final step (d) includes drying the fabrics in an automatic dryer at a temperature of at least about 38° C. This drying stage facilitates spreading of the fabric conditioning materials herein across the fabric surfaces and is especially useful when the particulate sorbitan ester material is utilized.

The following exemplifies the fabric conditioning compositions and methods of this invention and the benefits achieved by the utilization of such compositions and methods. These examples are illustrative of the invention herein and are not necessarily considered as limiting thereof.

EXAMPLE I

An imidazolinium salt essentially free of amines, amine salts and propoxylated imidazolinium salts is prepared in the following manner:

A. Diethylenetriamine and hardened tallow triglyceride in a molar ratio of amine/triglyceride of approximately 1.4/1 are added to a reaction vessel.

B. The amine and triglyceride are reacted for a period of three hours at a temperature of approximately 185° C. and atmospheric pressure.

C. The pressure in the reaction vessel is reduced to approximately 10 mm mercury and kept at that condition for a period of two hours. The product at this point is the imidazoline intermediate for the desired imidazolinium salt plus unreactants and primary and secondary amines from intermediate amide products. The reaction mixture is analyzed using conventional analytical techniques for the amount of imidazoline and primary and secondary amines.

D. The reaction vessel is cooled to 80° C. and isopropyl alcohol is added to the vessel in an amount equal to approximately 20% of the vessel's contents. The solvent aids in keeping the reaction medium fluid.

E. Propylene oxide is added to the reaction vessel in an amount equal to approximately 2% of the imidazoline and unreactants. This amount is sufficient to convert the unreacted primary and secondary amines to propoxylated tertiary amine.

F. The reaction vessel is subjected to a vacuum of approximately 10 mm mercury for a period of 1 hour.

G. The propoxylated reaction mixture is finally charged with an alkylating agent in the form of dimethylsulfate. The amount of alkylating agent originally used is slightly less than the number of moles of imidazoline formed after step C above. As the alkylation proceeds the pH of the reaction medium is monitored and additional dimethylsulfate is added until the pH is in the 5–7 range.

The product formed in the above reaction is 1-methyl-1-tallowamidoethyl-2-tallow imidazolinium methylsulfate which is essentially free of amines and amine salts.

EXAMPLE II

The following compositions are prepared:

|  | A | B |
|---|---|---|
| Imidazolinium salt of Example I | 26.25 grams | — |
| Imidazolinium salt of Example I made without employing the propylene oxide step | — | 26.25 grams |
| Aldehyde source | 0.55 grams | 0.55 grams |
| Water | q.s. to 1000 grams | q.s. to 1000 grams |

The pH of both samples are adjusted to 5.8 with sodium hydroxide.

Compositions A and B are analyzed for remaining aldehyde after one week at the temperatures shown below. The amount of aldehyde originally in the compositions is 550 ppm.

| Temperature | A | B |
|---|---|---|
| 70° F. | 510 ppm | 470 ppm |
| 100° F. | 508 | 401 |
| 120° F. | 464 | 346 |

The above figures demonstrate the improved aldehyde stability with the imidazolinium essentially free of amines and amine salts. Similar results are obtained with other imidazolinium salts made using polyamines and acylating or esterifying agents other than the diethylenetriamine and tallow triglyceride of Example I.

What is claimed is:

1. In a process for making quaternary imidazolinium salts having the following structure:

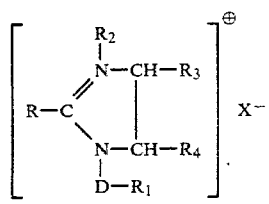

wherein R and $R_1$ are aliphatic groups having from about 10 to about 22 carbon atoms, $R_2$ is an alkyl or aralkyl group having from 1 to about 8 carbon atoms, $R_3$ and $R_4$ are hydrogen, hydroxy, short chain alkyl having from 1 to about 4 carbon atoms or hydroxy short chain alkyl having from 1 to about 4 carbon atoms, X is an anion and D is:

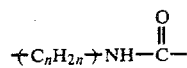

wherein n is a number from 1 to about 6; said process comprising the following steps:

A. Forming a mixture of an acylating or esterifying agent having an aliphatic hydrocarbon group containing from about 10 to about 22 carbon atoms associated with each acyl group and an alkylene or polyalkylene polyamine having two or three amino groups, one of which is a primary or secondary amino group in the 2 position with respect to a primary amino group, the molar ratio of acyl groups to primary amine and hydroxyl groups being from about 0.33:1 to about 1.5:1, B. Reacting the mixture of step A for a period of from about 3 to about 24 hours at a temperature of from about 100° C. to about 250° C. and then drawing a vacuum of from about 0.4 mm mercury to about 10 mm mercury for from about 1 to about 8 hours to form an imidazoline product in a mixture with starting materials and intermediates;

D. Treating the mixture of step B with an alkylating agent in an amount such that the molar ratio of alkylating agent to imidazoline is at least 1:1;

the improvement wherein, between said steps B and D, a step C is performed as follows:

C. Treating the imidazoline product mixture of step B with an alkoxylating agent, comprising an alkylene oxide selected from ethylene oxide, propylene oxide, butylene oxide, glycide, and cyclohexane oxide, in an amount equal to from about 1% to about 5% by weight of the imidazoline product mixture while maintaining the temperature at from about 80° C. to about 140° C. for a period of from about 0.5 to about 8 hours;

whereby to form a composition comprising quaternary imidazolinium salts which are essentially free of primary and secondary amines, amine salts and alkoxylated imidazolinium salts.

2. The process of claim 1 wherein the molar ratio of acyl groups to primary amine and hydroxyl groups in step A is from about 0.33 to 0.66 and the following step is inserted between steps B and C:

Reacting the imidazoline product mixture of step B with an acylating or esterifying agent of the type in step A in a molar ratio of acyl groups to imidazoline product from about 1:1 to about 1.5:1, at a temperature of from about 100° C. to about 250° C. and for a period of from about 1 to about 24 hours.

3. The process of claim 1 wherein the molar ratio of acyl groups to primary amine and hydroxyl groups is from about 0.67 to about 1.50.

4. The process of claim 3 wherein an organic solvent in an amount equal to from about 1% to about 25% by weight of the imidazoline product mixture of step B is added along with the alkoxylating agent in step C.

5. The process of claim 4 wherein the aliphatic or cycloaliphatic hydrocarbon group associated with the acylating or esterifying agent in step A has from about 14 to about 20 carbon atoms.

6. The process of claim 5 wherein the alkylene or polyalkylene polyamine in step A has the formula:

NH₂—CH₂—CH₂NH—X wherein X is selected from the group consisting of $+CH_2-CH+_nOH$, $+CH_2-CH_2+_nCH_3$, hydrogen and $+CH_2-CH_2+_nNH_2$ wherein n is a number from 1 to about 6.

7. The process of claim 6 wherein the acylating or esterifying agent in step A is a glyceride ester of tallow fatty acid.

8. The process of claim 7 wherein the alkylene or polyalkylene amine in step A is diethylenetriamine.

9. The process of claim 8 wherein the alkylating agent is dimethylsulfate.

10. In a process for making quaternary imidazolinium salts having the following structure:

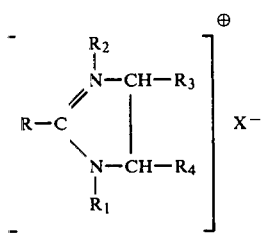

wherein R and $R_1$ are aliphatic hydrocarbon groups having from about 10 to about 22 carbon atoms, $R_2$ is an alkyl or aralkyl group having from 1 to about 8 carbon atoms, $R_3$ and $R_4$ are hydrogen, hydroxy, short chain alkyl having from 1 to about 4 carbon atoms or hydroxy short chain alkyl having from 1 to about 4 carbon atoms and X is an anion; said process comprising the following steps:

A. Forming a mixture of an acylating or esterifying agent having an aliphatic hydrocarbon group containing from about 10 to about 22 carbon atoms associated with each acyl group and an alkylene or polyalkylene polyamine having two or three amino groups, one of which is a primary or secondary amino group in the 2 position with respect to a primary amino group, the molar ratio of acyl groups to primary amine and hydroxyl groups being from about 0.33:1 to 1.5:1;

B. Reacting the mixture of step A for a period of from about 3 to about 24 hours at a temperature of from about 100° C. to about 250° C. and then drawing a vacuum of from about 0.4 mm mercury to about 10 mm mercury for from about 1 to about 8 hours to form an imidazoline product in a mixture with starting materials and intermediates;

D. Treating the mixture of step B with an alkylating agent in an amount such that the molar ratio of alkylating agent to imidazoline is at least 1:1;

the improvement wherein, between said steps B and D, a step C is performed as follows:

C. Treating the imidazoline product mixture of step B with an alkoxylating agent, comprising an alkylene oxide selected from ethylene oxide, propylene oxide, butylene oxide, glycide, and cyclohexane oxide, in an amount equal to from about 1% to about 5% by weight of the imidazoline product mixture while maintaining the temperature at from about 80° C. to about 140° C. for a period of from about 0.5 to about 8 hours;

whereby to form a composition comprising quaternary imidazolinium salts which are essentially free of primary and secondary amines, amine salts and alkoxylated imidazolinium salts.

11. The process of claim 10 wherein the molar ratio of acyl groups to primary amine and hydroxyl groups in step A is from about 0.33 to 0.66 and the following step is inserted between steps B and C;

Reacting the imidazoline product mixture of step B with an acylating or esterifying agent of the type in step A in a molar ratio of acyl groups to imidazoline product of from about 1:1 to about 1.5:1, at a temperature of from about 100° C. to about 250° C. and for a period of from about 1 to about 24 hours.

12. The process of claim 10 wherein the molar ratio of acyl groups to primary amine and hydroxyl groups is from about 0.67 to about 1.50.

13. The process of claim 12 wherein an organic solvent in an amount equal to from about 1% to about 25% by weight of the imidazoline product mixture of step B is added along with the alkoxylating agent in step C.

14. The process of claim 13 wherein the aliphatic or cycloaliphatic hydrocarbon group associated with the acylating or esterifying agent in step A has from about 14 to about 20 carbon atoms.

15. The process of claim 14 wherein the alkylene or polyalkylene polyamine in step A has the formula:

NH₂—CH₂—CH₂—NH—X wherein X is selected from the group consisting of $+CH_2-CH+_nOH$, $+CH_2-CH_2+_nCH_3$, hydrogen and $+CH_2-CH_2+_nNH_2$ wherein n is a number from 1 to about 6.

16. The process of claim 15 wherein the acylating or esterifying agent in step A is a glyceride ester of tallow fatty acid.

17. The process of claim 16 wherein the alkylene or polyalkylene amine in step A is diethylenetriamine.

18. The process of claim 17 wherein the alkylating agent is dimethylsulfate.

* * * * *